United States Patent [19]

Chan et al.

[11] Patent Number: 5,368,610
[45] Date of Patent: Nov. 29, 1994

[54] USE OF METAL SALTS AND CHELATES TOGETHER WITH CHLORITES AS OXIDANTS IN HAIR COLORING

[75] Inventors: Alexander Chan, Mineola, N.Y.; Gottfried Wenke, Woodbridge, Conn.; Ciuseppe Prota, Napoli, Italy

[73] Assignee: Clairol Incorporated, Stamford, Conn.

[21] Appl. No.: 49,708

[22] Filed: Apr. 20, 1993

[51] Int. Cl.$^5$ ................................. A61K 7/13
[52] U.S. Cl. ........................... 8/406; 8/405; 8/408; 8/409; 8/423; 8/623; 8/624; 8/628
[58] Field of Search ................ 8/405, 406, 407, 408, 8/416, 421, 410, 409, 423, 623, 624, 628

[56] References Cited

U.S. PATENT DOCUMENTS

| | | | |
|---|---|---|---|
| 2,934,396 | 4/1960 | Charle et al. | 8/11 |
| 3,214,472 | 10/1965 | Charle et al. | 260/571 |
| 3,236,734 | 2/1966 | Charle et al. | 167/88 |
| 4,904,274 | 2/1990 | Schultz et al. | 8/406 |
| 5,032,138 | 7/1991 | Wolfram et al. | 8/412 |
| 5,131,911 | 7/1992 | Lang et al. | 8/405 |
| 5,173,085 | 12/1992 | Brown et al. | 8/405 |
| 5,199,954 | 4/1993 | Schultz et al. | 8/405 |

FOREIGN PATENT DOCUMENTS 2028818 12/1970 Germany.

*Primary Examiner*—Paul Lieberman
*Assistant Examiner*—Caroline L. Dusheck
*Attorney, Agent, or Firm*—Charles J. Zeller

[57] ABSTRACT

The invention provides methods, compositions and kits for oxidative hair dyeing utilizing an oxidative hair dye precursor, and an alkali metal chlorite together with a water soluble copper, iron, manganese or cobalt salt, a chelate of said salts or a mixture of said salts and chelates.

25 Claims, No Drawings

USE OF METAL SALTS AND CHELATES TOGETHER WITH CHLORITES AS OXIDANTS IN HAIR COLORING

RELATED APPLICATION

This specification describes certain improvements in the invention described and claimed in copending and commonly owned patent application Ser. No. 07/875,874 filed Apr. 29, 1992 and in U.S. Pat. No. 5,032,138, also commonly owned.

FIELD OF THE INVENTION

The present invention relates to compositions, methods and kits for dyeing hair. More specifically, the invention relates to methods of dyeing hair using oxidizable hair dye precursors in which the oxidation is conducted in the presence of at least one selected chlorite salt together with selected redox metal salts, chelates of such salts and mixtures of said salts and/or chelates. The invention relates also to compositions for conducting the hair dyeing processes and to the packaged reactants sold in the form of a kit.

BACKGROUND OF THE INVENTION

Modern hair dyeing methodology has developed from its initiation in the 1950's to the point where, today it is the third largest product type in the hair care category following shampoos and conditioners.

A wide variety of hair dyes or colorants have been developed by the art. These include direct dyes, autoxidative dyes, oxidative dyes and dyes which achieve their desired effect by conversion to a melanin. These latter dyes include dihydroxyphenylalanine (DOPA) 5,6-dihydroxyindole (DHI) and related compounds such as 5,6-dihydroxyindole carboxylic acid (DHICA) and its lower alkyl esters as well as N-lower alkyl derivatives of these compounds and acyloxy analogs such as 5,6-diacetoxyindole (DAI).

The most commonly used method of dyeing hair, particularly human hair, is oxidative dyeing in which a mixture of aromatic compounds, generally of the benzenoid series, containing a plurality of amino and hydroxy functions, which are themselves colorless, are converted by coupling reactions and oxidative processes, both known to those skilled in the art, to a blend of colored compounds within the hair fibers. The colorless aromatic compounds, in a suitable base formulation, normally are mixed with hydrogen peroxide or other strong oxidizing agent shortly before use. The colored compounds or dyes, typically, are formed by oxidative coupling between primary intermediates (usually diaminobenzenes or aminophenols) and couplers which are phenols or related cyclic compounds. Different shades are developed by using a mixture containing more than one of both the intermediate and the coupler.

It is also known to dye hair with certain compounds which, while they are useful as primary intermediates in association with couplers, may also be used alone since they may be directly oxidized either with an oxidizing agent or, with certain of the more sensitive compounds, by exposure to air. The oxidized primary intermediate can couple with unoxidized primary intermediate to form a dye.

Another recently developed method for dyeing hair involves formation of melanin-like pigments by oxidative conversion of appropriate precursors. The fundamental chemistry underlying this innovative technology is discussed in detail by G. Prota in Melanins and Melanogenesis, Academic Press, San Diego (1992). The principal melanin precursors employed by the art are DHI and its analogs including, for example, DHICA and its lower alkyl and alkaryl esters such as methyl, ethyl and benzyl esters and DAI. These, and other DHI analogs are hair dye precursors which may be oxidized to melanin under known conditions.

All of the foregoing compounds may be considered as oxidative hair dye precursors, in that under appropriate oxidizing conditions they will oxidize to form hair dyes or colorants.

It is well known that oxidative dyeing of hair can be achieved by first mixing a solution of dye precursors with a solution of oxidant (usually hydrogen peroxide or a salt which forms hydrogen peroxide). The final mixture is then applied directly to hair fibers. While this is the standard procedure for dyeing hair suggested by existing products in the market, it is not without disadvantages. The major concern is the destructive damage of hair during the dyeing process.

To circumvent this shortcoming, German DE 2,028,818 suggests metal pretreatment of hair. This enables the user to shorten the dyeing time. As a result, damage to hair may be minimized. However, such treatment is insufficient for total elimination of damage to hair induced by peroxide.

U.S. Pat. No. 5,100,436 describes the use of 2,2'-dipyridyl and o-phenanthroline metal ion chelates in hair dye mixtures utilizing hydrogen peroxide or oxidizing agents which function by the production of hydrogen peroxide.

In U.S. Pat. No. 5,032,138, use of a chlorite in lieu of hydrogen peroxide is suggested. The process significantly reduces oxidative damage of hair. The drawbacks of this method are that the color of the treated hair tends to be weak, a long period of time is thus necessary to produce a desired color intensity, and a large molar excess of chlorite is required.

The art, therefore, is constantly seeking more convenient dyeing methods which can be used with all types of oxidative dye precursors without damaging the hair. According to the present invention, it has been found that certain redox metal salts such as copper, iron, manganese, or cobalt salts can be used in combination with chlorite to dye hair. This, on the one hand, avoids the oxidative damage of hair, and, on the other hand, affords more intense and rapid coloring of hair than if chlorite is used alone.

SUMMARY OF THE INVENTION

It has now been discovered that oxidative hair dye precursors can be oxidized to hair dyes utilizing an oxidizing mixture which contains an alkali metal chlorite together with water soluble salts or chelates of selected redox metals such as those formed from copper, iron, manganese or cobalt. Accordingly, the invention comprises aqueous hair dyeing compositions containing the selected hair dyeing precursors together with the oxidizing mixture. It relates also to methods for the use of such compositions to dye hair as well as to packages or kits containing such compositions.

There are many advantages to the compositions and methods of this invention. These include:

1. The desired hair color can be attained in a shorter period of time (about 5 to 10 minutes) compared to the use of chlorite without a metal salt as taught in U.S. Pat. No. 5,032,138 cited above.

2. Chlorite salts do not bleach or cause other oxidative damage to human hair as does hydrogen peroxide.

3. The actual coloring of the hair can be performed at a pH of from 6 to 9, although some variation is possible, rather than under the strongly basic conditions associated with the use of hydrogen peroxide-ammonia or amine combinations.

4. The amount of chlorite oxidizing agent employed may be as much as 80% less than is required when the reaction is conducted without the use of metals. This aspect of the invention is specifically illustrated in Examples 23 and 24.

Sodium chlorite is the preferred alkali metal chlorite for use in the compositions of this invention. It is non-toxic, the $LD_{50}$ value in rats being 165 mg/kg. Moreover, it does not degrade the dyes formed by the coupling reaction, thus permitting better utilization of the ingredients.

DEFINITIONS

As used in the specification, the terms listed below have the meanings discussed or defined.

By "permanent" is meant a color not removable by shampooing with a conventional surfactant-containing shampoo, the permanency being attributable to the formation of molecules too large to be removed from the hair.

By "melanin" is meant a synthetically derived pigment formed by polymerization of a melanin-forming precursor such as DHI.

By "oxidative hair dye precursor" or "hair dye precursor" is meant a compound or combination of compounds which can be oxidized in an aqueous composition containing alkali metal chlorites together with salts, chelates, salt/chelate or chelate/chelate mixtures of redox metals such as copper, iron, manganese or cobalt.

By "treatment" is meant contacting the hair to be dyed with a hair dye composition of the invention. The composition employed may be formed separately from the hair and then applied. It may also be formed by mixing the separate reactants as they are applied to the hair, for example by mixing the streams from separate aerosol containers as the streams are applied to the hair. They may also be formed by contacting the reactants with the hair to be treated as the reactants are applied to the hair, either concurrently or successively.

The term "aqueous composition" is employed herein in its usual generic sense as embracing any water-containing composition useful for the present purposes. This includes true solutions of the oxidizing mixture and the hair dye precursor in an aqueous medium, either alone or in conjunction with other materials which are also dissolved or dispersed in the aqueous medium. The term aqueous composition also encompasses any mixture of the oxidizing agent and the hair dye precursor either alone or with other ingredients. The various components may be colloidally dispersed or may merely be intimately mixed therein. Moreover, the aqueous composition may comprise water or water together with an additional or auxiliary solvent. Typical auxiliary solvents which may be used to enhance the solubility of the components include lower alkanols such as ethanol, propanol and isopropanol; carbitol; propylene glycol; ethylene glycol; diethylene glycol; monoethyl ether; glycerine; and the like.

The term "oxidative dye" includes compounds and mixtures of compounds which can be oxidized under the conditions described herein to form hair colorants. It includes, for example, primary intermediates either alone or together with one or more couplers, autoxidative dyes, and melanin forming dyes such as DHI and its analogs.

By "a tinctorially effective amount" is meant that quality of a hair dye which will produce a permanent color change in human hair. It will, of course, vary with the hair dye precursor selected and its concentration as well as the method of treatment and other factors readily evaluated by the skilled artisan.

The term "package" as employed herein is used in the widest possible sense. It includes retail packages with the separate components of the final composition packaged in the same box or in separate boxes, but sold together in a kit. It also includes separate compositions in large amounts such as might be sold to a beauty salon whether or not the separate compositions are sold in the same container and are intended to be used together.

The compositions of this invention are particularly adapted for co-dispensing from a compartmentalized package, such as the containers described in U.S. Pat. Nos. 3,241,722 and 4,103,772, the disclosures of which are incorporated herein by reference. Such co-dispensing container packages have been previously employed with hydrogen peroxide dye systems. In such co-dispensing containers, the reactants are normally stored in separate compartments of the container. The containers are constructed with means for mixing the reactants in the container and means for dispensing the reactions mixture.

Mixing is generally accomplished by one of the following procedures. One method employs an aerosol package and valve adapted so that the compositions in the compartments mix as they pass through the valve. In the other method, a frangible partition is provided between the separate compartments and the container is formed with a mechanism which permits the partition to be pierced, or otherwise broken, so that the compositions mix prior to dispensing. Depending upon the design of the container, the resulting mixed composition can be dispensed under aerosol pressure, by simple pouring or by any other convenient method.

When such co-dispensing containers are employed with hydrogen peroxide systems, there is always danger of premature mixing because of accidental leakage through the partition. As a result the dye forming reaction, which is intended to take place in the open air takes place in a closed container and may result in explosive pressure. There is less danger when the oxidative salts of this invention are employed since the dye forming reaction does not generate oxygen.

It will be apparent to the skilled artisan, as the description of this invention progresses, that dye combinations can be usefully employed in the compositions of this invention. Such combinations include, for example, primary intermediates with or without couplers together with DHI or a DHI analog.

DETAILED DESCRIPTION OF THE INVENTION

The compositions of this invention are applied either to living human hair or to human hair implanted in a wig or other artificial device. They will comprise a carrier vehicle, usually water, or water containing a lower alkanol such as ethanol or isopropanol to aid solubility, together with a tinctorially effective amount of the selected oxidative hair dye precursor, including mixtures (hereinafter sometimes identified as the reactants) and from about 0.05 to 20%, preferably 0.1 to 6% of alkali metal chlorite salt together with from about 0.001% to 5%, preferably 0.01% to 1% of a water soluble metal salt of a redox metal such as a copper, iron, manganese or cobalt salt or a chelate of such salts. On a molar basis, the amount of chlorite salt employed is only about 20% to 30% of the amount employed in the absence of the metal catalyst.

All percent by weights defined in this disclosure and claims are percents by weight based on the total weight of the composition.

In contrast to the results achieved according to the process of the above identified U.S. Pat. No. 5,032,138 the process of this invention provides much more intense colors in a shorter time.

Several alternate variations of the procedure are possible.

For example, the hair may first be treated with the selected metal salt solution and thereafter treated with a mixture containing the oxidizing agent and the oxidative dye precursor. This procedure is illustrated in Example 1.

Alternatively, the hair may be initially treated with a mix containing the metal salt or chelating agent and the oxidative dye precursor, and this treatment followed by soaking the hair in a solution of the oxidizing agent. This procedure is illustrated in Example 15. A similar procedure without the chelating agent is illustrated in Examples 16 and 17.

Examples 2-6, 9-14 and 22 illustrate processes of the invention in which all of the ingredients are applied to the hair in one composition.

It is also possible to develop color in a post treatment step. In this case, the dye precursors are allowed to penetrate into the hair and the hair is rinsed before the oxidant and the selected metal salts and chelating agents are applied to the hair.

The use of alkali metal chlorite as an oxidant in combination with DHI or other melanin precursors is described in the above identified patent application Ser. No. 07/875,874. In the process of that application, the oxidative polymerization of DHI to melanin occurs at a relatively slow rate which allows the DHI to penetrate into the hair before conversion to melanin takes place. In accordance with this invention, the oxidative polymerization rate is greatly increased. Accordingly in a typical procedure of the invention, the hair is first treated with the melanin precursor for a sufficient period to permit penetration of the hair (usually, about 5 to 30 minutes) and thereafter with the other reactants of the invention. The hair may be rinsed between treatments to remove excess melanin precursor. Typically, the time period for the second treatment is from about 2 to 5 minutes. The oxidative color development is advantageously combined with a shampoo since it is generally desirable to terminate hair coloring process with a shampoo.

With less reactive melanin precursors, for example DHICA, it is possible to apply the precursor to the hair simultaneously with the chlorite and metal catalyst.

Hair dye products of the invention may contain oxidative dye precursors comprising mixtures of primary intermediates and couplers together with products which may be oxidized to form melanin. With these compositions, the dye precursors are allowed to penetrate the hair and the hair color is developed by treatment with the other reactants in compositions which may contain a surfactant so that the oxidizing composition also functions as a shampoo.

The amount of oxidative dye precursors employed in the practice of this invention will be about the same as utilized in conventional oxidant hair dye compositions. The amounts which will be tinctorially effective will vary with the selected reactants and other factors, as described above. Since the amounts will not vary appreciably from those employed with ordinary oxidant compositions containing hydrogen peroxide, the skilled artisan will have no difficulty in selecting the amounts of hair dye precursor to be employed. Generally precursor will be present in an amount of from about 0.1% to 10%, preferably 0.5% to 5%.

The skilled artisan will recognize that the percentages for the various ingredients as given above refer to the amounts of the ingredients in the compositions as they are mixed and applied to the hair. The various ingredients may be prepared as separate compositions each containing the selected components in appropriate amounts so that when the compositions are mixed and the resulting mixture applied to the hair, the mixture will contain the various reactants in the stated amounts. As will be clear from this disclosure, the separate compositions may be applied to the hair successively rather than simultaneously.

With most oxidative dyes, the oxidant will be separately formulated for use to form a mixture with the other components just prior to use or as it is used. This is more fully illustrated in the examples. Thus, a product of the invention may comprise a package containing two separate units of aqueous compositions, one containing the oxidant, the other containing an oxidative dye precursor together with the selected metal salt, chelate or mixture thereof.

It will be apparent that there are several packaging possibilities and several different compositions which may be employed in the practice of this invention. Important commercial compositions of the invention include those which function both as oxidants and shampoos. These compositions are employed when the oxidizing step is conducted subsequent to treatment of the hair with the oxidative dye precursor. The compositions will contain the oxidant and sufficient surfactant to achieve a hair cleaning effect. It may also contain the metal salt chelate or mixture. The amount of oxidant, salt or chelate in the compositions will be in the ranges indicated above. The amount of surfactant will be the amount normally employed in shampoos. Typically the composition will contain up to about 10% surfactant, preferably from about 1% to 5%.

The surfactant may be selected from any of a wide variety of anionic, cationic or non-ionic surfactants normally employed in shampoos. They include, for example sodium lauryl sulfate, ammonium lauryl sulfate, isoceteth-20, lanolin linoleate, polysorbate-20 and PPG-10 lanolin alcohol ether (CTFA Dictionary Nomenclature).

These compositions are especially important because they permit the oxidation reaction and hair cleaning to take place in one step.

Any of the conventional oxidizable primary intermediates and coupling agents used with ordinary oxidant compositions for hair coloring can be employed in the compositions of this invention to achieve a wide variety of tints and hues.

A large number of such primary intermediates are known including, for example, para-phenylenediamines, corresponding to the formula:

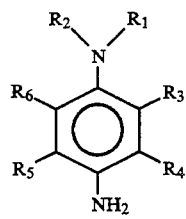

in which:

$R_1$ and $R_2$, which may be identical or different, denote hydrogen, a $C_1$–$C_6$ lower alkyl group, a $C_1$–$C_6$ alkyl radical substituted with one or more hydroxy group(s) or with a methoxy, substituted amino, methylsulphonylamino or aminocarbonyl group, a furfuryl group, or a phenyl radical optionally substituted with an amino group; $R_3$ and $R_6$ denote, independently of one another, hydrogen, a $C_1$–$C_6$ lower alkoxy group, a halogen atom such as a chlorine, a $C_1$–$C_6$ lower alkyl group, or a $C_1$–$C_6$ lower alkyl group substituted with one or more hydroxy group(s): and $R_4$ and $R_5$ denote, independently of one another, hydrogen, a $C_1$–$C_6$ lower alkoxy group, a $C_1$–$C_6$ lower alkyl group, or a halogen atom such as chlorine, as well as their salts with inorganic or organic acids, N,N'-diphenylalkylenediamines in which the phenyl groups are substituted at the para position with an OH or amino group optionally substituted with a $C_1$–$C_6$ alkyl group, it being possible for the amino groups joined by the alkylene group to be substituted with $C_1$–$C_6$ alkyl $C_1$–$C_6$ hydroxyalkyl or $C_1$–$C_6$ aminoalkyl, para-aminophenols, ortho-aminophenols, ortho-phenylenediamines and substituted, aromatic heterocyclic compounds. Preferably no more than two of the R-values are other than hydrogen in a specific compound.

Among the useful compounds of formula (I), there may be mentioned p-phenylenediamine, 2-methyl-p-phenylenediamine, 2-methoxy-p-phenylenediamine, 2-chloro-N-methyl-p-phenylenediamine, N-furfuryl-p-phenylenediamine, 3-methoxy-$N^1$-methyl-p-phenylenediamine, 2-chloro-p-phenylenediamine, N-methyl-p-phenylenediamine, 2,3-dimethyl-p-phenylenediamine, 3-chloro-$N^1$-methyl-p-phenylenediamine, 3-methyl-$N^1$,$N^1$-dimethyl-p-phenylenediamine, 2-[N-ethyl-N-(4-amino-3-methyl)-phenyl]amino-5-methyl-$N^1$-ethyl-$N^1$-(methylsulphonylaminoethyl)-p-phenylenediamine, N-(2-methoxyethyl)-p-phenylenediamine, 2,6-dimethyl-p-phenylenediamine, N,N-bis(2-hydroxyethyl)-p-phenylenediamine. The N,$N^1$-diphenylalkylenediamines includes, for example N,$N^1$-bis(2-hydroxyethyl)-N,$N^1$-bis(p-aminophenyl)ethylenediamine. Their salts with acids such as the monohydrochlorides, dihydrochlorides or sulphates are also suitable.

Among ortho primary intermediates, o-aminophenol, 5-chloro-o-aminophenol and ortho-phenylenediamine are preferred.

Among heterocyclic primary intermediates, it is preferred, according to the invention, to use 2,3-diamino-6-methoxypyridine, 2-(2-hydroxyethyl)amino-5-aminopyridine, 2-methylamino-3-amino-6-methoxypyridine, 2,5-diaminopyridine, 2-hydroxyethylamino-5-amino pyridine, and 2-[(N,N-bis(hydroxyethyl)-]amino-5-aminopyridine.

More especially preferred primary intermediates are p-phenylenediamine, 2-methyl-p-phenylenediamine,N-(2-methoxyethyl)-p-phenylenediamine, N,N-bis(2-hydroxyethyl)-p-phenylenediamine and p-aminophenol.

Among couplers or colour modifiers, there may be mentioned, in particular, the compounds corresponding to the formula:

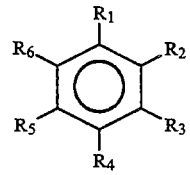

in which:

$R_1$ denotes hydroxy or an amino group which can be substituted with one or more $C_1$–$C_6$ hydroxyalkyl groups; $R_3$ and $R_5$, independently of one another, can denote hydrogen, a hydroxy group, an amino group optionally substituted with a $C_1$–$C_6$ lower hydroxyalkyl group or a $C_1$–$C_6$ lower alkyl group; and $R_2$, $R_4$ and $R_6$ can denote a hydrogen atom or a $C_1$–$C_6$ alkoxy group, a hydroxyalkoxy group or a $C_1$–$C_6$ lower alkyl group; it also being possible for $R_3$ and $R_4$ to, together, form a methylenedioxy group.

Among suitable couplers, there may be mentioned 2-methoxy-5-aminophenol, 2-methoxy-5-[N-(2-hydroxyethyl) amino]phenol, 1,3-diamino-2,6-dimethoxybenzene, 2-methoxy-1-(N-methylamino)-4-(2-hydroxyethoxy)-3-aminobenzene, 1,5-diamino-2-methoxybenzene, 1,5-diamino-2,4-dimethoxybenzene, 2,4-dimethoxy-1,5-bis(2-hydroxyethyl)aminobenzene, 2,6-dimethoxy-3-(2-hydroxyethyl)amino]phenol, 2,6-dimethyl-3-aminophenol, 4-ethoxy-3-[N,N-bis(2-hydroxyethylamino)]aniline, 2-(2,4-diaminophenoxy)ethanol, 4-methoxy-3-hydroxyethylaminoaniline, 4,5-methylenedioxy-2-methoxyphenol, 5-amino-2-methyl-phenol, 4,5-methylenedioxy-2-methoxyaniline, 3-aminophenol, 1,3-dihydroxybenzene, 4-(hydroxyethoxy)-1,3-phenylenediamine, 2,4-(dihydroxyethoxy)-1,5-phenylenediamine, 1,3-phenylenediamine, 2-methyl-1,3-dihydroxybenzene, mono- or polyhydroxylated derivatives of naphthalene and of aminonaphthalene, pyrazolones and benzomorpholines.

Other suitable couplers are 6-aminobenzomorpholine, 1-amino-7-naphthol, 6-hydroxybenzomorpholine, 1-naphthol, 1,3-dihydroxynaphthalene and 1,2-dihydroxybenzene.

Among heterocyclic couplers there may be mentioned 2,6-dihydroxypyridine, 2,6-diaminopyridine, 2-amino-4-hydroxypyridine, 2-hydroxy-4-aminopyridine, 2-amino-6-hydroxypyridine and the like. Included also are further derivatives of 2,6-diamino alkyl pyridines wherein the amino nitrogen of one or both amino groups is mono- or disubstituted with a $C_1$–$C_6$ alkyl group such as the methyl, propyl, isopropyl, butyl, iso- or sec-butyl, pentyl, sec-pentyl, neopentyl, t-butyl, hexyl, 3-methyl-pentyl or 4-methyl-pentyl groups. The amino groups of either the 2-amino-4-hydroxy- or 2-hydroxy-4-amino-pyridines may also have mono- or di-$C_1$–$C_6$ alkylation on the nitrogen atoms.

The 2,6-diamino-, or 4-amino-2-hydroxy- or 2-amino-4-hydroxy pyridine nitrogens may also, either singularly or doubly, be derivatized with alkoxy substituents having carbon lengths of 1 to 6 with specific mention of 2-hydroxyethyl, 3-hydroxypropyl, 4-hydroxybutyl, 5-hydroxypentyl, 6-hydroxyhexyl, 2-hydroxypropyl, 2-hydroxybutyl, 2-hydroxypentyl, 2-hydroxyhexyl, 3-hydroxybutyl, 3-hydroxypentyl, 2-hydroxyhexyl, 4-hydroxypentyl and 5hydroxypentyl groups.

Among substituted 1,2-dihydroxybenzenes, 4-methyl1,2dihydroxybenzene and 3-methoxy1,2-dihydroxybenzene are especially preferred.

The aminohydroxybenzenes are chosen, in particular, from 2-amino-4-methoxyphenol, 2-aminophenol, 2,4-dimethoxy-5-amino-1-hydroxybenzene, 5-amino-2-methylphenol, 3-amino-phenol, 3-amino-4 methylphenol and their salts.

By way of example of suitable triaminobenzenes there may be mentioned 1,5-diamino-2-methyl-4-(p-hydroxyphenyl)aminobenzene and its salts.

Table 1 below lists some of the preferred primary intermediates and couplers for use in this invention.

TABLE 1

| Primary Intermediates: | p-phenylenediamine<br>p-aminophenol<br>o-aminophenol<br>N,N-bis(2-hydroxyethyl)-p-phenylenediamine<br>2,5-diaminopyridine<br>2,5-toluenediamine |
|---|---|
| Couplers: | resorcinol<br>m-aminophenol<br>1-naphthol<br>5-amino-o-cresol<br>2-methylresorcinol<br>2,4-dihydroxyethoxy-1,5-phenylenediamine<br>m-phenylenediamine |

Autoxidative dyes which may be employed in the invention include:
1,2,4-trihydroxybenzene
2,5-diaminoanisole Melanin precursors which are useful for dyeing hair according to the process of this invention include DHI and its analogs.

All of the dyes employed in the practice of this invention are conventional and well known. However, this should not be regarded as a limitation of the invention.

The metal salts employed in this invention include salts such as water soluble copper (cuprous and cupric), iron (ferrous and ferric), manganese and cobalt salts. Chelates of these salts may also be employed. If such chelates are used, the salt itself need not be soluble so long as it is solubilized by the chelating agent. The amount of salt or chelate in the compositions as applied to the hair is from about 0.001% to 10%, preferably 0.01% to 2%.

Any of a number of non-toxic chelating agents normally employed in cosmetic compositions may be utilized in this invention. These include by way of example only, ethylenediamine tetra-acetic acid and its various salts as well as ascorbic acid, succinic acid, dipyridyl, tartaric acid, tris-hydroxymethylaminomethane, citric acid and 2,4-pentanedione.

Chelating agents are the preferred catalysts for use in this invention since this retain the metallic ions in solution. Metallic salts may precipitate from solution as hydroxide at elevated pH values or as salts with the anions of certain buffers, e.g. phosphate buffers.

Well known conventional additives usually employed in oxidative hair coloring compositions, such as thickeners, surface active agents, antioxidants and fragrances may be included in the compositions of the invention.

Such compositions are preferably solutions, but they may be in the form of emulsions, suspensions, lotions, or gels.

Surface active agents employed in the dyeing compositions of this invention can be anionic, nonionic, cationic or amphoteric. By way of examples of the various types of surface active agents, there can be mentioned: higher alkylbenzene sulfonates; alkylnaphthalenesulfonates, sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants include: sodium lauryl sulfate; polyoxyethylene lauryl ester; myristyl sulfate; glyceryl monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethylbenzylammonium chloride; dodecylbenzene sodium sulfonate; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate and the sodium salt of 3-diethyl-tridecanol-6-sulfate and the like. The quantity of surface active agent can vary over a wide range, such as from about 0.05% to 30% and preferably from about 0.10 to 10%.

A thickening agent may also be incorporated in the dyeing composition of this invention. The thickener which may be one or several of those commonly used in hair dyeing. These are exemplified by such products as sodium alginate or gum arabic, or cellulose derivatives, such as methylcellulose e.g.. Methocel 60 HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of thickening agent can also vary over a wide range, even as high as 20%. Ordinarily it will range from about 0.5 to 5%. The viscosity of the composition may vary from about 1 cp to about 100,000 cps. For a typical lotion formulation, composition viscosity is from about 100 cps to about 10,000 cps.

It may also be useful to incorporate an antioxidant in the present dye compositions. A variety of antioxidants known in the prior art would be useful for this purpose. Among these mention may be made of the inorganic sulfites, e.g., sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc. The quantities of antioxidant employed can vary appreciably. However, the concentration will, in general, be up to about 1%, typically 0.001 to 1%.

The aqueous dyeing compositions of this invention can be prepared by conventional methods used in the hair dyeing art. Thus, they can be prepared by dissolving or suspending the components in the selected media with adequate mixing. Preparation may take place at ambient temperatures, i.e., 20° to 35° C., but solubility and rate of preparation can be enhanced utilizing elevated temperatures, for example, 40° to 100° C.

A particular advantage of the compositions of this invention compared to similar compositions which do not contain metal salts, as in U.S. Pat. No. 5,032,138, or chelates, is the rapidity with which they impart desired color tones to the human hair. This feature is of special interest to high volume beauty salons where customer turnover is an important economic factor. It is also important to the individual user, whether the dye be applied personally or professionally.

The skilled artisan will recognize that, while the components of the compositions of this invention are applied to the hair to be dyed essentially concurrently, i.e. within a sufficiently short period of time so that each component has its desired effect, they may be applied in any of several alternative orders. For example, the hair may be treated successively with aqueous compositions, the first containing the metal salt or chelate, the second containing the dye, and the third containing the oxidant. Alternatively, the dye and the oxidant may be combined in the second composition. Other variations of the order of treatment are possible. All are included within the scope of the invention.

The following examples are illustrative of this invention. They illustrate the advantages of the compositions of the invention over the compositions of U.S. Pat. No. 5,032,138 which, though similar to the compositions of this invention, do not contain metal salts or chelates and require a longer dyeing period in order to have the same color intensity on hair. Additionally, the use of metal catalysts permit the use of smaller quantities of the oxidant.

The tristimulus values in the examples are standard Hunter chromaticity values obtained by procedures well known to those skilled in the art. The values recorded manifest the ability of the compositions of the invention to be usefully employed in hair coloring processes.

In the Hunter Tristimulus System, L is a measure of lightness and darkness, that is, the depth of the color of the hair tress. The lower the value of L the darker the color. A decrease in the value of L indicates a darkening of the hair tress. In the case of bleached and blended gray hair, a lowering of L shows deposition of hair dye on the tress.

The a value is a measure of the greenness or redness of the hair's color. As the a value increases, the hair has a more prominent red tonality. A lowering in the a value results in greener shades. The b value is a measure of the yellow and blue color. Higher b values indicate a more yellow hue in the hair.

The various buffer solutions employed in the examples were prepared as follows:

A pH 7 buffer was prepared by mixing 82.3 mL of 0.2M sodium phosphate dibasic solution and 17.7 mL of 0.1M citric solution.

B pH 8 Tris (hydroxymethyl)aminomethane buffer was prepared by combining 15.9 mL of 0.2M of the base with 10 mL of 0.2M HCl. The final volume was adjusted to 50 mL with distilled water.

C pH 9 Tris(hydroxymethyl)aminomethane buffer was prepared by combining 50 mL of 0.2M of the base with 4.33 mL of 0.2M HCl. The final volume was adjusted to 100 mL with distilled water.

EXAMPLE 1

A blended gray hair tress was first soaked for 5 minutes in one of the 1% metal salt solutions identified in Table 2. It was then rinsed and treated with the following dye composition for an additional 5 minutes:

| p-Phenylenediamine | 0.11% |
| 5-Amino-o-cresol | 0.14% |
| Sodium chlorite | 1.25% |
| Ethanol (95%) | 12.5% |
| Buffer C qs | 100% |

The dyed tress was shampooed and rinsed with water. As a control, hair was treated with the same dye compositions for 20 minutes, but without the metal ion pretreatment. The results are set forth in Table 2.

TABLE 2

| Catalyst | Tristimulus Values of Dyed Swatches | | |
|---|---|---|---|
| | L | a | b |
| Control | 19.8 | 5.2 | 1.6 |
| FeCl$_3$ | 19.1 | 6.0 | 1.4 |
| CuSO$_4$ | 17.2 | 4.3 | 1.2 |
| FeSO$_4$ | 16.5 | 4.4 | 0.8 |
| AlCl$_3$ | 23.9 | 5.0 | 3.2 |

Even though treated for only 10 minutes the copper and iron salts afforded darker hair colors than the control which was treated for 20 minutes. On the other hand, the aluminum salt, the use of which is disclosed in DE 2,028,818 cited above was not found to be effective.

EXAMPLE 2

Blended gray hair tresses were treated with the following compositions containing the metal salts listed in Table 3 for 5 minutes, shampooed, and rinsed. A red-violet color was imparted to the hair. As a control experiment, no metal salt was used and the tress was dyed for 20 minutes.

| p-Phenylenediamine | 0.11% |
| 5-Amino-o-cresol | 0.14% |
| Sodium chlorite | 1.25% |
| Metal salt | 0.15% |
| EDTA disodium salt | 0.1% |
| Ethanol (95%) | 12.5% |
| Buffer C qs | 100% |

The results are set forth in Table 3 below:

TABLE 3

| Catalyst | Tristimulus Values of Dyed Swatches | | |
|---|---|---|---|
| | L | a | b |
| Control | 21.4 | 5.0 | 2.8 |
| FeCl$_3$ | 20.2 | 3.8 | 2.0 |
| CuSO$_4$ | 21.1 | 4.1 | 1.9 |
| FeSO$_4$ | 21.0 | 3.8 | 2.2 |
| AlCl$_3$ | 26.5 | 2.1 | 4.8 |

It is clear that the iron and copper salts were effective as dye adjuvants. The aluminum salt was not.

EXAMPLE 3

A tress of Piedmont hair was treated with the following composition:

| N,N-bis(2-hydroxyethyl)-p-phenylenediamine | 0.368% |

-continued

| | |
|---|---|
| dihydrochloride | |
| 5-Amino-2-methylphenol | 0.165% |
| EDTA tetrasodium salt | 0.1% |
| Ferric chloride hexahydrate | 0.15% |
| Ethanol | 12.5% |
| Sodium chlorite | 0.5% |
| Buffer C q.s. | 100.0% |

The hair was shampooed and rinsed with water after 5 minutes. A violet color was imparted on the fibers.

EXAMPLE 4

A tress of blended gray hair was treated with the following composition:

| | |
|---|---|
| P-Aminophenol | 0.136% |
| m-Aminophenol | 0.146% |
| EDTA tetrasodium salt | 0.1% |
| Ferric chloride hexahydrate | 0.15% |
| Ethanol | 12.5% |
| Sodium chlorite | 0.5% |
| Buffer C q.s. | 100.0% |

The hair was shampooed and rinsed with water after 5 minutes. A golden brown color was imparted on the fibers. If no ferric chloride was used in the above composition, it imparted a grayish brown color on hair in 5 minutes. Tristimulus values of the two swatches are recorded in the following.

| Method | L | a | b |
|---|---|---|---|
| Control (5 min.) | 29.4 | 0.6 | 6.8 |
| Metal catalyzed | 24.6 | 1.5 | 6.7 |

EXAMPLE 5

A tress of blended gray hair was treated with the following composition for 5 minutes:

| | |
|---|---|
| P-Aminophenol | 0.25% |
| m-Aminophenol | 0.26% |
| Cobalt acetate.4H$_2$O | 0.05% |
| Sodium chlorite (80%) | 1.00% |
| Ethanol (95%) | 12.5% |
| Buffer C q.s. | 100.0% |

The dyed hair was then shampooed and rinsed with water. In the control experiment, no cobalt acetate was used in the above composition. Tristimulus values of the two swatches demonstrate that the solution containing the metal salt affords a darker color (i.e., smaller L value) than the control.

| | L | a | b |
|---|---|---|---|
| catalyzed | 15.1 | 1.0 | 5.2 |
| control | 26.8 | 0.8 | 5.2 |

EXAMPLE 6

Blended gray hair was treated with the following composition for 5 minutes.

| | |
|---|---|
| p-Phenylenediamine | 0.135% |
| Resorcinol | 0.147% |
| Manganese chloride | 0.05% |
| Sodium chlorite (80%) | 0.50% |
| Ethanol (95%) | 12.5% |
| Buffer C q.s. | 100.0% |

The dyed hair was then shampooed and rinsed with water.

In the control experiment, no manganese chloride was used in the above composition. Tristimulus values of the two swatches demonstrate that the solution containing the metal salt affords a darker color (i.e., smaller L value) than the control.

| | L | a | b |
|---|---|---|---|
| catalyzed | 25.5 | 0.6 | 5.3 |
| control | 29.0 | 0.4 | 6.1 |

The following Examples 7 and 8 illustrate the distinction between the catalytic efficiency of the metal salts of this invention compared to lead, zinc, and aluminum salts. While these latter salts are good catalysts for the hydrogen peroxide dyeing system, they have no effect on the current invention.

EXAMPLE 7

Blended gray hair was first pretreated with a 1% aqueous solution of lead acetate for 5 minutes. This pretreated hair was then soaked in either composition A and B for an additional 5 minutes. Control swatches were prepared by treating the hair with either solution A and B without the metal ion pretreatment also for 5 minutes.

| | | |
|---|---|---|
| Solution A: | p-Phenylenediamine | 0.108% |
| | 5-Amino-o-cresol | 0.17% |
| | Sodium chlorite (80%) | 0.50% |
| | Ethanol (95%) | 6.25% |
| | Buffer C q.s. | 100.0% |
| Solution B: | p-Phenylenediamine | 0.108% |
| | 5-Amino-o-cresol | 0.17% |
| | Hydrogen peroxide (6%) | 50.0% |
| | Ethanol (95%) | 6.25% |
| | Buffer C q.s. | 100.0% |

The dyed hair was shampooed and rinsed with water. Tristimulus values given below show that lead enhances the color intensity on hair only in the peroxide system.

| | | L | a | b |
|---|---|---|---|---|
| Solution A | catalyzed | 29.9 | 1.2 | 5.3 |
| | control | 29.4 | 1.4 | 5.2 |
| Solution B | catalyzed | 21.3 | 3.0 | 3.1 |
| | control | 23.6 | 4.1 | 2.7 |

EXAMPLE 8

A hair dye solution was prepared according to the following:

| | |
|---|---|
| p-Phenylenediamine | 0.35% |
| 5-Amino-2-methylphenol | 0.4% |
| Propylene glycol | 10.0% |
| EDTA Tetrasodium salt | 0.3% |
| Sodium sulfite | 0.6% |
| Sodium chlorite | 0.75% |
| Metal catalyst | 0.04% |

-continued

| | |
|---|---|
| Buffer C q.s. | 100.0% |

The above solution was used to treat blended gray hair for 5 minutes, and the dyed tress was shampooed and rinsed thoroughly with water. Tristimulus values of the dyed swatches are given in the following table:

| Metal used | L | a | b |
|---|---|---|---|
| nil | 23.0 | 4.5 | 2.9 |
| FeSO$_4$ | 20.2 | 4.2 | 1.6 |
| ZnSO$_4$ | 23.6 | 4.9 | 3.0 |

EXAMPLE 9

Blended gray hair was treated with the following composition for 5 minutes.

| | |
|---|---|
| p-Phenylenediamine | 0.25% |
| m-Aminophenol | 0.26% |
| Cobalt acetate.4H$_2$O | 0.05% |
| Sodium chlorite (80%) | 1.00% |
| Ethanol (95%) | 12.5% |
| Buffer B q.s. | 100.0% |

The dyed hair was shampooed and rinsed with water.

The control hair tress was prepared by dyeing the hair with the above solution containing no cobalt salt for 5 minutes.

Tristimulus values given below indicate that the catalysed system imparts darker color on hair.

| | L | a | b |
|---|---|---|---|
| catalyzed | 23.5 | 1.6 | 4.5 |
| control | 24.9 | 0.8 | 4.5 |

EXAMPLE 10

Blended gray hair was treated with the following composition for 5 minutes.

| | |
|---|---|
| p-Phenylenediamine | 0.325% |
| m-Aminophenol | 0.33% |
| Ferrous sulfate.7H$_2$O | 0.025% |
| Sodium Ethylenediamine-tetra-acetate | 0.30% |
| Sodium chlorite (80%) | 1.00% |
| Ethanol (95%) | 12.5% |
| Buffer A q.s. | 100.0% |

The dyed hair was shampooed and rinsed with water.

The control hair tress was prepared by dyeing the hair with the above solution containing no iron salt for 5 minutes.

Tristimulus values given below indicate that the catalyzed system imparts darker color on hair.

| | L | a | b |
|---|---|---|---|
| catalyzed | 17.4 | 1.7 | 2.0 |
| control | 21.9 | 0.8 | 4.2 |

Blended gray hair was treated with the following composition for 5 minutes.

| | |
|---|---|
| p-Phenylenediamine | 0.136% |
| m-Aminophenol | 0.146% |
| Ferrous chloride | 0.15% |
| Sodium Ethylenediamine-diacetate | 0.10% |
| Sodium chlorite (80%) | 0.60% |
| Ethanol (95%) | 12.5% |
| Buffer A q.s. | 100.0% |

The dyed hair was shampooed and rinsed with water.

The control hair tress was prepared by dyeing the hair with the above solution containing no iron salt for 5 minutes.

Tristimulus values given below indicate that the catalyzed system imparts darker color on hair.

| | L | a | b |
|---|---|---|---|
| catalyzed | 24.6 | 1.5 | 6.7 |
| control | 29.4 | 0.6 | 6.8 |

EXAMPLE 12

Blended gray hair was treated with the following composition for 5 minutes.

| | |
|---|---|
| p-Phenylenediamine | 0.2954% |
| Resorcinol | 0.3225% |
| Ferrous sulfate.7H$_2$O | 0.050% |
| Bipyridyl | 0.08% |
| Sodium chlorite (80%) | 1.00% |
| Ethanol (95%) | 12.5% |
| Buffer C q.s. | 100.0% |

The dyed hair was shampooed and rinsed with water.

The control hair tress was prepared by dyeing the hair with the above solution containing no iron salt for 5 minutes.

Tristimulus values given below indicate that the catalysed system imparts darker color on hair.

| | L | a | b |
|---|---|---|---|
| catalyzed | 25.2 | 0.6 | 5.0 |
| control | 26.5 | 0.6 | 5.2 |

EXAMPLE 13

Blended gray hair was treated with the following composition for 5 minutes.

| | |
|---|---|
| p-Phenylenediamine | 0.295% |
| Resorcinol | 0.3225% |
| Ferrous acetylacetonate | 0.050% |
| Sodium chlorite (80%) | 1.00% |
| Ethanol (95%) | 12.5% |
| Buffer C q.s. | 100.0% |

The dyed hair was shampooed and rinsed with water.

The control hair tress was prepared by dyeing the hair with the above solution containing no iron salt for 5 minutes.

Tristimulus values given below indicate that the catalysed system imparts darker color on hair.

| | L | a | b |
|---|---|---|---|
| catalyzed | 25.4 | 0.9 | 5.2 |

|         | L    | a   | b   |
|---------|------|-----|-----|
| control | 26.5 | 0.6 | 5.2 |

EXAMPLE 14

A composition was prepared by mixing 2 parts of Solution 1 with 1 part of Solution 2. This composition was used to treat blended gray hair for 5 minutes.

| Solution 1 | Sodium laureth sulfate | 15.0% |
|---|---|---|
|  | Cetyl alcohol | 2.0% |
|  | Nonoxynol-4 | 6.0% |
|  | Oleic acid | 13.0% |
|  | Octoxynol-1 | 12.0% |
|  | Lauramide DEA | 3.0% |
|  | Propylene glycol | 10.0% |
|  | Carbital | 4.0% |
|  | AMP | 4.0% |
|  | Isopropyl alcohol | 9.0% |
|  | p-Phenylenediamine | 0.5% |
|  | m-Aminophenol | 0.51% |
|  | Ferric acethylacetonate | 0.1% |
|  | Water q.s. |  |
| Solution 2 | Sodium chlorite | 4.0% |
|  | Water q.s. | 100.0% |

A light brown color was imparted on the hair after shampoo.

EXAMPLE 15

Hair can also be pretreated with a combination of metal salt and dye intermediates, followed by soaking in the chlorite solution. This again produces a more intense color on hair than the control, which is dyed by soaking in a solution containing both dye intermediates and sodium chlorite for 5 minutes.

Solution A was first used to treat blended gray hair for 5 minutes. The hair was rinsed with water briefly, blotted dry, and was kept in Solution B for another 5 minutes to afford a light brown color.

| Solution A | p-Phenylenediamine | 0.33% |
|---|---|---|
|  | m-Aminophenol | 0.34% |
|  | Copper sulfate.5H2O | 0.13% |
|  | Monoethanolamine q.s. pH = 9 |  |
|  | Water q.s. | 100.0% |
| Solution B | Sodium chlorite | 1.33% |
|  | Buffer C q.s. | 100.0% |

The control swatch was obtained by treating the hair with a mixture of equal parts of Solutions A and B except that Solution A did not contain the copper salt. A weaker color on the control swatch was obvious.

|           | L    | a   | b   |
|-----------|------|-----|-----|
| catalyzed | 24.5 | 1.4 | 4.5 |
| control   | 26.8 | 0.8 | 5.2 |

Similarly, hair can be first treated with suitable metal salt solutions before dyeing. In all cases, darker color than the control was obtained on hair.

EXAMPLE 16

A swatch of blended gray hair was first soaked in a 1% solution of ferrous sulfate for 5 minutes. The tress was rinsed briefly with water and was then treated with the following dye composition for another 20 minutes.

| p-Phenylenediamine | 0.108% |
|---|---|
| 5-Amino-2-methylphenol | 0.135% |
| Ethanol | 12.5% |
| Sodium chlorite | 0.625% |
| Buffer B q.s. | 100.0% |

The control swatch was prepared by dyeing the blended gray hair for 20 minutes with the above solution without the metal salt pretreatment. It is obvious from the table that the metal salt pretreatment method is more superior.

| Method | L | a | b |
|---|---|---|---|
| Control | 21.7 | 6.0 | 3.1 |
| Metal pretreated | 16.5 | 4.4 | 0.8 |

EXAMPLE 17

A swatch of blended gray hair was first soaked in a 1% alkaline solution of copper sulfate for 5 minutes. The tress was rinsed briefly with water and was then treated with the following dye composition for another 20 minutes.

| p-Phenylenediamine | 0.108% |
|---|---|
| 5-Amino-2-methylphenol | 0.135% |
| Ethanol | 12.5% |
| Sodium chlorite | 0.625% |
| Buffer B q.s. | 100.0% |

The control swatch was prepared by dyeing the blended gray hair for 20 minutes with the above solution without the metal salt pretreatment. It is obvious from the table that the metal salt pretreatment method is superior.

| Method | L | a | b |
|---|---|---|---|
| Control (20 min.) | 22.6 | 6.0 | 3.2 |
| Metal pretreated | 17.2 | 4.3 | 1.2 |

EXAMPLE 18

A tress of blended gray hair was treated with a solution, containing 2-Methyl-DHI (1%), i-PrOH (12%) and buffer C for 15 minutes. The hair was rinsed briefly with water and was then exposed to a short post-treatment (2 minutes) with the following composition:

| sodium chlorite | 1.00% |
|---|---|
| $FeSO_4 \times 7\ H_2O$ | 0.02% |
| $Na_4$-EDTA | 0.3% |
| Phosphate buffer (pH 7) q.s. | 100.0% |

The dyed hair was rinsed, shampooed and dried. The color of the hair was medium to dark brown.

|  | L | a | b |
|---|---|---|---|
| Hunter Tristimulus values | 24.8 | 1.1 | 2.9 |

If the catalyst ($FeSO_4$ and $Na_4$-EDTA) was omitted in otherwise identical treatment.

|  | L | a | b |
|---|---|---|---|
| Hunter Tristimulus values color gray-brown | 27.7 | 0.8 | 4.4 |

EXAMPLE 19

A tress of blended gray hair was treated with a solution, containing 5,6-Dihydroxyindoline hydrobromide salt (1%), i-PrOH (12%) and buffer C for 15 minutes. The hair was rinsed briefly with water and was then exposed to a short post-treatment (2 minutes) with the composition of Example 18.

The dyed hair was rinsed, shampooed and dried. The color of the hair was ash-brown.

|  | L | a | b |
|---|---|---|---|
| Hunter Tristimulus values | 22.3 | 0.6 | 3.0 |

If the catalyst (FeSO$_4$ and Na$_4$-EDTA) was omitted in otherwise identical treatment.

|  | L | a | b |
|---|---|---|---|
| Hunter Tristimulus values color gray-brown | 24.5 | 0.7 | 4.1 |

EXAMPLE 20

A tress of blended gray hair was treated with a solution, containing DHICA (1%), i-PrOH (12%) and buffer C for 15 minutes. The hair was rinsed briefly with water and was then exposed to a short post treatment (2 minutes) with the composition of Example 18. The dyed hair was rinsed, shampooed and dried. The color of the hair was dark gray.

|  | L | a | b |
|---|---|---|---|
| Hunter Tristimulus values | 28.4 | 0.5 | 5.2 |

If the catalyst (FeSO$_4$ and Na$_4$-EDTA) was omitted in otherwise identical treatment, the values were as follows:

|  | L | a | b |
|---|---|---|---|
| Hunter Tristimulus values color gray-brown | 29.3 | 0.4 | 5.3 |

EXAMPLE 21

A tress of blended gray hair was treated with a solution, containing DHICA (0.6%), DHI (0.4%), i-PrOH (12%) and buffer C for 15 minutes. The hair was rinsed briefly with water and was then exposed to a short post-treatment (2 minutes) with the composition of Example 4. The dyed hair was rinsed, shampooed and dried. The color of the hair was dark ash-brown.

|  | L | a | b |
|---|---|---|---|
| Hunter Tristimulus values | 23.3 | 0.7 | 2.4 |

If the catalyst (FeSO$_4$ and Na$_4$-EDTA) was omitted in otherwise identical treatment, the values were as follows:

|  | L | a | b |
|---|---|---|---|
| Hunter Tristimulus values color dary gray | 26.6 | 0.7 | 3.9 |

EXAMPLE 22

This example demonstrates the use of chlorite and a catalyst in a one step dyeing process of the invention.

A tress of blended gray hair was treated with the following composition for 5 minutes:

| 2-Me-DHI | 1.0% |
|---|---|
| sodium chlorite | 3.0% |
| FeSO$_4$ × 7 H$_2$O | 0.02% |
| Na-EDTA | 0.3% |
| i-PrOH | 12.0 |
| phosphate buffer (pH 7) q.s. | 100.0% |

The dyed hair was rinsed, shampooed and dried. The color of the hair was brown.

|  | L | a | b |
|---|---|---|---|
| Hunter Tristimulus values | 24.4 | 1.7 | 3.2 |

If the catalyst (FeSO$_4$ and Na$_4$-EDTA) was omitted in otherwise identical treatment.

|  | L | a | b |
|---|---|---|---|
| Hunter Tristimulus values | 28.5 | 1.1 | 5.8 |

EXAMPLE 23

The following composition was prepared and used to treat blended gray hair for 10 min. The colored swatch was shampooed and rinsed with water. This dyed swatch served as a control.

|  | wt. % |
|---|---|
| p-Phenylenediamine | 0.325 |
| m-Aminophenol | 0.33 |
| Ethanol (95%) | 12.5 |
| EDTA tetrasodium salt | 0.30 |
| Sodium chlorite | 10.0 |
| Buffer C q.s. | 100.0 |

A series of additional compositions each containing 0.025% of FeSO$_4$.H$_2$O and lesser amounts of chlorite as indicated in the following table were prepared. Each solution was used to treat separate swatches of blended gray hair using the same procedure as with the control. Table 4 below shows the tristimulus values of all dyed tresses. It is obvious that the color on the catalyzed swatches was more intense than the control even though more oxidant was used in the control experiment.

TABLE 4

Tristimulus values of tresses dyed with and witout the catalyst.

| Amount of oxidant | L | a | b |
| --- | --- | --- | --- |
| 10.0% (control) | 21.0 | 0.8 | 3.9 |
| 7.5% | 16.7 | 1.9 | 2.0 |
| 5.0 | 17.8 | 2.5 | 1.8 |
| 2.5% | 15.7 | 2.3 | 1.2 |
| 1.0% | 14.1 | 2.6 | 0.8 |
| 0.2% | 17.0 | 2.4 | 1.5 |

EXAMPLE 24

A control swatch was prepared by treating piedmont hair with the following solution for 10 min. The dyed hair was shampooed and rinsed thoroughly with water.

| | |
| --- | --- |
| 4-Amino-o-cresol | 0.37% |
| 5-Amino-o-cresol | 0.375% |
| Ethanol (95%) | 12.5% |
| EDTA tetra sodium salt | 0.30% |
| Sodium chlorite (80%) | 5.0% |
| Buffer C q.s. | 100.0% |

The experimental swatches were similarly dyed by the same composition except for the addition of 0.025% of FeSO$_4$.H$_2$O and the amounts of sodium chlorite shown in Table 5.

TABLE 5

Tristimulus values of tresses dyed with and without the catalyst.

| Amount of oxidant | L | a | b |
| --- | --- | --- | --- |
| 5.0% (control) | 45.2 | 7.3 | 16.8 |
| 4.0% | 41.2 | 10.6 | 15.7 |
| 1.0% | 42.0 | 12.2 | 16.5 |
| 0.5% | 42.0 | 12.5 | 16.8 |
| 0.2% | 40.9 | 14.7 | 17.7 |
| 0.0% | 51.5 | 5.0 | 18.2 |

Again it is clear that more intense color is obtained with the metal salt containing compositions even though they contain smaller amounts of the oxidizing agent than the controls.

What is claimed is:

1. An aqueous hair dye composition containing from about 0.05% to 20% by weight of an alkali metal chlorite; from about 0.001% to 5% of a water soluble copper, iron, manganese or cobalt salt, a chelate of said salt, or a mixture thereof together with an amount of an oxidative hair dye precursor which will oxidize to form a tinctorially effective amount of a hair dye.

2. A composition as in claim 1 wherein the hair dye precursor is a mixture containing an oxidative primary intermediate and a coupler.

3. A composition as in claim 1 wherein the hair dye precursor is dihydroxyindole or an analog thereof which will oxidize to form melanin.

4. A composition as in claim 1 wherein the hair dye precursor is a primary intermediate.

5. A composition as in claim 1 wherein the hair dye precursor is a mixture containing an oxidative primary intermediate and a coupler together with dihydroxyindole or an analog thereof which will oxidize to form melanin.

6. A composition as in claim 1 wherein the alkali metal chlorite is sodium chlorite.

7. A composition as in claim 1, 2, 3, 4, 5 or 6 wherein the amount of alkali metal chlorite is from 0.1% to 6% by weight.

8. A package comprising in separate containers a first aqueous composition containing sodium chlorite and a second aqueous composition containing an amount of at least one hair dye precursor which is oxidizable to form a tinctorially effective amount of a hair dye, a metal salt being present in either of said first or said second compositions or alternatively being present in the package in a separate container as a third composition, said compositions being adapted for application to hair either separately or as an admixture of two or more of said compositions, the amount of sodium chlorite in the first composition, the amount of hair dye precursor in the second composition, and the amount of metal salt in the first, second or third composition being sufficient so that when applied to hair, whether separately or in admixture, the concentration of sodium chlorite is from about 0.05 to 20%, the concentration of the hair dye precursor is from about 0.1 to 10%, and the concentration of the metal salt is from about 0.001 to 5%, all percents being on a weight basis, the metal salt, being selected from the group consisting of water-soluble copper, iron, manganese or cobalt salts, chelates of said salts, and mixtures thereof.

9. A package as in claim 8 wherein the hair dye precursor is a mixture containing an oxidative primary intermediate and a coupler.

10. A package as in claim 8 wherein the hair dye precursor is dihydroxyindole or an analog thereof which will oxidize to form melanin.

11. A package as in claim 8 wherein the hair dye precursor is a primary intermediate.

12. A package as in claim 8 wherein the hair dye precursor is a mixture containing an oxidative primary intermediate and a coupler together with dihydroxyindole or an analog thereof which will oxidize to form melanin.

13. A package as in claim 8 wherein the amount of sodium chlorite is from 0.1% to 6% by weight.

14. The package of claim 8 wherein the metal salt is present in the first composition.

15. The package of claim 8 wherein the metal salt is present in the third composition.

16. A method for permanently dyeing hair which comprises
    (a) contacting the hair with an aqueous composition containing from about 0.05% to about 20% by weight of an alkali metal chlorite; from about 0.001% to 5% of a water soluble copper, iron, manganese or cobalt salt, a chelate of said salt, or a mixture thereof together with an amount of hair dye precursor which will oxidize to form a tinctorially effective amount of a hair dye and,
    (b) permanently coloring the hair by allowing said hair dye precursor to oxidize.

17. A method as in claim 16 wherein the hair dye precursor is a mixture containing an oxidative primary intermediate and a coupler.

18. A method as in claim 16 wherein the hair dye precursor is dihydroxyindole or an analog thereof which will oxidize to form melanin.

19. A method as in claim 16 wherein the hair dye precursor is a primary intermediate.

20. A method as in claim 16 wherein the hair dye precursor is a mixture containing an oxidative primary intermediate and a coupler together with dihydroxyindole or an analog thereof which will oxidize to form melanin.

21. A method as in claim 16 wherein the alkali metal chlorite is sodium chlorite.

22. A method as in claim 16, 17, 18, 19, 20 or 21 wherein the amount of alkali metal chlorite is from 0.1% to 6% by weight.

23. A method for permanently dyeing hair comprising:
   (a) first contacting the hair with a first aqueous composition containing (i) a metal salt, or (ii) a hair dye precursor, or (iii) a mixture of a metal salt and a hair dye precursor, and
   (b) thereafter contacting the hair with a second aqueous composition containing sodium chlorite, said second aqueous composition further containing (i) a metal salt when composition (a)(ii) is first applied or (ii) a hair dye precursor when composition (a)(i) is first applied;
   (c) the metal salt being selected from the group consisting of water-soluble copper, iron, manganese or cobalt salts, chelates of said salts, and mixtures thereof, and the hair dye precursor being oxidizable to form a tinctorially effective amount of a hair dye;
   (d) the concentration of the hair dye precursor in the first or second composition as the case may be being from 0.1 to 10%; the concentration of the metal salt in the first or second composition as the case may be being from 0.001 to 5%, and the concentration of the sodium chlorite in the second composition being from 0.05 to 20%, all percents being on a weight basis.

24. A method as in claim 23, wherein the hair dye precursor is a mixture containing an oxidative primary intermediate and a coupler.

25. A method as in claim 23, wherein the hair dye precursor is dihydroxyindole or an analog thereof which will oxidize to form melanin.

* * * * *